(12) United States Patent
Yoshida et al.

(10) Patent No.: US 10,725,283 B2
(45) Date of Patent: Jul. 28, 2020

(54) LIGHT SOURCE APPARATUS

(71) Applicant: OLYMPUS CORPORATION, Tokyo (JP)

(72) Inventors: Yusuke Yoshida, Hachioji (JP); Yutaka Shirota, Hino (JP); Masaaki Watanabe, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 458 days.

(21) Appl. No.: 15/786,731

(22) Filed: Oct. 18, 2017

(65) Prior Publication Data
US 2018/0136454 A1   May 17, 2018

Related U.S. Application Data

(63) Continuation of application No. PCT/JP2016/053904, filed on Feb. 10, 2016.

(30) Foreign Application Priority Data

Apr. 24, 2015   (JP) .................................. 2015-089708

(51) Int. Cl.
*G02B 23/24* (2006.01)
*A61B 1/06* (2006.01)
(Continued)

(52) U.S. Cl.
CPC ...... *G02B 23/2453* (2013.01); *A61B 1/00045* (2013.01); *A61B 1/00112* (2013.01);
(Continued)

(58) Field of Classification Search
CPC ........................... G02B 23/2453; G02B 23/26; G02B 23/2469; A61B 1/06; A61B 1/128;
(Continued)

(56) References Cited

U.S. PATENT DOCUMENTS

| 8,803,056 B2 | 8/2014 | Shirota et al. |
| 2014/0054450 A1 | 2/2014 | Shirota et al. |
| 2016/0037999 A1* | 2/2016 | Yabe ..................... A61B 1/0638 600/109 |

FOREIGN PATENT DOCUMENTS

| CN | 103619234 A | 3/2014 |
| EP | 2702928 A1 | 3/2014 |

(Continued)

OTHER PUBLICATIONS

International Search Report dated May 17, 2016 issued in PCT/JP2016/053904.

*Primary Examiner* — Tony Ko
(74) *Attorney, Agent, or Firm* — Scully, Scott, Murphy & Presser, P.C.

(57) ABSTRACT

An optical sensor that detects intensity of light is disposed, inside an optical case, at a position that allows the optical sensor to receive light other than light received by a lens system, out of light emitted by an LED. The optical sensor is housed in a dedicated photometric case. The photometric case is provided with a light guide portion that includes a transmission part and a shielding part. The transmission part is disposed in an optical path of light that directly travels from the LED to the optical sensor and allows transmission of the light. The shielding part blocks indirect light that is reflected or scattered inside the optical case, from entering the optical sensor. Accordingly, it is possible to accurately detect only the light in the direct optical path from the LED.

9 Claims, 15 Drawing Sheets

(51) Int. Cl.
  *G02B 23/26* (2006.01)
  *A61B 1/00* (2006.01)
  *A61B 1/04* (2006.01)
  *A61B 1/12* (2006.01)

(52) U.S. Cl.
  CPC .................. *A61B 1/04* (2013.01); *A61B 1/06* (2013.01); *A61B 1/0646* (2013.01); *A61B 1/0684* (2013.01); *A61B 1/128* (2013.01); *G02B 23/2469* (2013.01); *G02B 23/26* (2013.01)

(58) Field of Classification Search
  CPC ....... A61B 1/0684; A61B 1/0646; A61B 1/04; A61B 1/00112; A61B 1/00045
  See application file for complete search history.

(56) References Cited

FOREIGN PATENT DOCUMENTS

| | | | |
|---|---|---|---|
| EP | 2976989 | A1 | 1/2016 |
| JP | 5393935 | B1 | 1/2014 |
| JP | 2015019695 | A | 2/2015 |
| WO | 2013150897 | A1 | 10/2013 |
| WO | 2015005277 | A1 | 1/2015 |

\* cited by examiner

LIGHT SOURCE APPARATUS

CROSS REFERENCE TO RELATED APPLICATION

This application is a continuation application of PCT/JP2016/053904 filed on Feb. 10, 2016 and claims benefit of Japanese Application No. 2015-089708 filed in Japan on Apr. 24, 2015, the entire contents of which are incorporated herein by this reference.

BACKGROUND OF THE INVENTION

1. Field of the Invention

The present invention relates to a light source apparatus that detects emission intensity of light emitted by a light source while applying the light to an object.

2. Description of the Related Art

Some of existing light source apparatuses that supply, to an endoscope and the like, light applied to an object adopt a system that measures a quantity of light emitted by a light source in order to adjust the quantity of the light of the light source, and the measured light quantity is fed back to a control section to control the light quantity to an appropriate amount.

For example, Japanese Patent No. 5393935 discloses a light source apparatus that can detect light emission intensity of a light emitting device under light of higher light emission intensity without decreasing a light quantity of illumination light supplied to an endoscope.

Further, Japanese Patent Application Laid-Open Publication No. 2015-19695 discloses a light source apparatus that makes it possible to perform control to stop emission of illumination light without need for manual operation and the like in a case where an insertion state of a probe is not suitable for emission of the illumination light.

SUMMARY OF THE INVENTION

A light source apparatus according to an aspect of the present invention includes: a light source portion including a first light source emitting light applied to an object, and a second light source that emits light applied to the object and is higher in light emission intensity than the first light source; a first optical portion configured to receive a portion of the light emitted by the first light source, and to form an optical path to apply the received light to the object; a second optical portion configured to receive a portion of the light emitted by the second light source, and to form an optical path to apply the received light to the object; a detection portion that is disposed at a position allowing the detection portion to receive light other than the light received by the first optical portion, out of the light emitted by the first light source, and is configured to detect intensity of the received light; a shielding part that is disposed between the first light source and the detection portion, to block indirect light that is generated by reflection or scattering of the light emitted by the first light source, from entering the detection portion, and is configured to block the light; and a transmission part that is disposed at a position apart from the second light source with respect to the first light source in an optical path of light that directly enters the detection portion out of the light within a maximum distribution angle of the first light source, and is configured to allow transmission of the light.

A light source apparatus according to another aspect of the present invention includes: a light source portion configured to emit light applied to an object; an optical portion configured to receive a portion of the light emitted by the light source portion, and to form an optical path to apply the received light to the object; a detection portion that is disposed at a position allowing the detection portion to receive light other than the light received by the optical portion, out of the light emitted by the light source portion, and is configured to detect intensity of the received light; a transmission part including an opening part in an optical path of the light directly entering the detection portion, out of light within a maximum distribution angle of the light source portion; a shielding part disposed between the light source portion and the detection portion to block indirect light that is generated by reflection or scattering of the light emitted by the light source portion, from entering the detection portion; a housing in which the light source portion and the optical portion are disposed; and a heat transfer portion that is configured to transfer heat of the detection portion and is disposed outside the housing.

A light source apparatus according to still another aspect of the present invention includes: a light source portion configured to emit light applied to an object; an optical portion configured to receive a portion of the light emitted by the light source portion, and to form an optical path to apply the received light to the object; a detection portion that is disposed at a position allowing the detection portion to receive light other than the light received by the optical portion, out of the light emitted by the light source portion, and is configured to detect intensity of the received light; a transmission part including an opening part in an optical path of light directly entering the detection portion, out of light within a maximum distribution angle of the light source portion; and a shielding part disposed between the light source portion and the detection portion to block indirect light that is generated by reflection or scattering of the light emitted by the light source portion, from entering the detection portion. A substrate on which the detection portion is mounted and a substrate on which a driving device driving the light source portion is mounted are electrically connected to each other through fitting of terminals of the respective substrates. One of the terminals of the respective substrates includes a fitting part, a mounting part, and a coupling part. The fitting part is fitted to another terminal, the mounting part is mounted on the substrate, and the coupling part couples the fitting part with the mounting part and is displaced with smaller force than force of the fitting part by vibration load.

DETAILED DESCRIPTION OF THE PREFERRED EMBODIMENT(S)

Embodiments of the present invention are described below with reference to drawings.

First Embodiment

Figure 1:
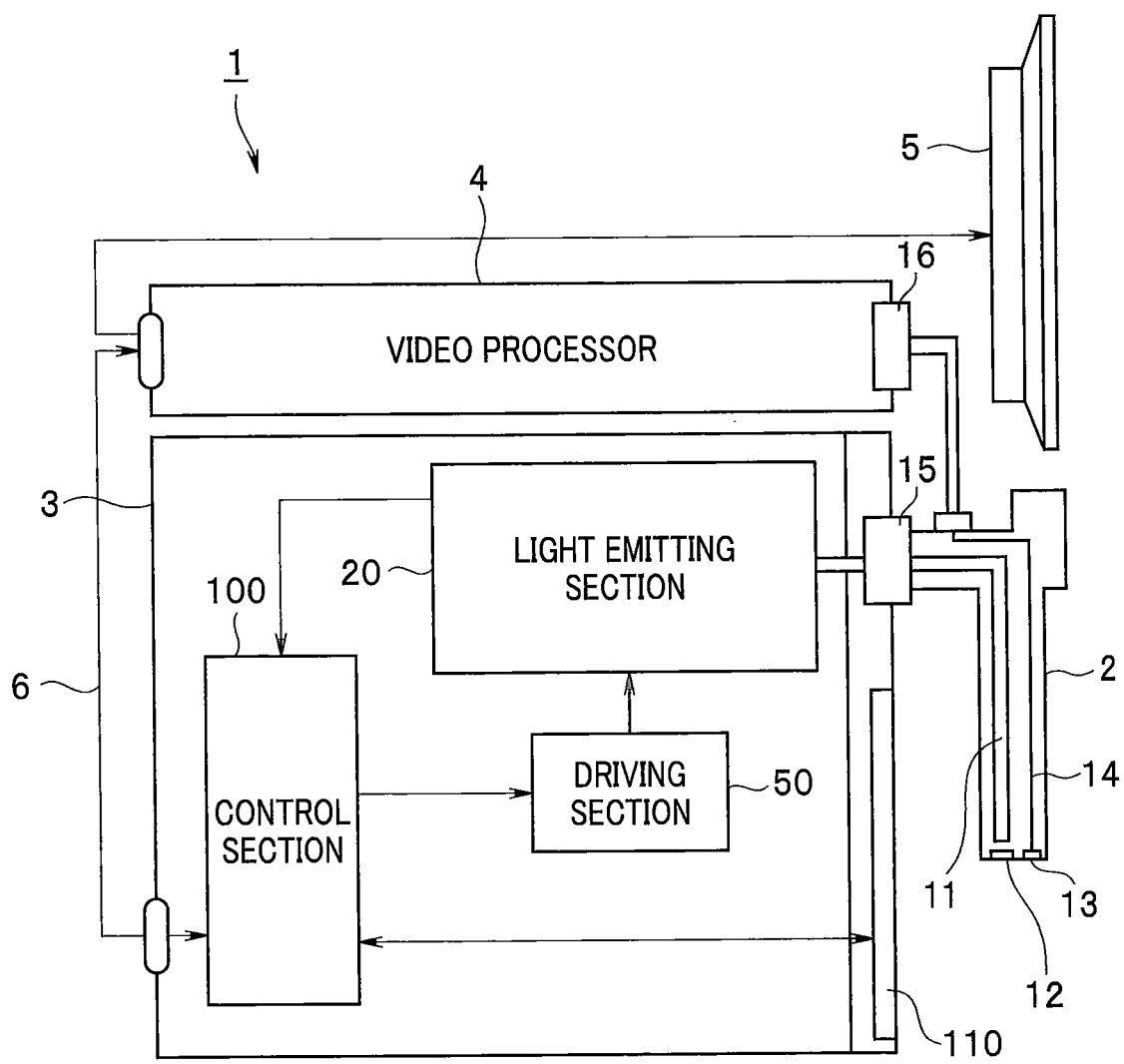
FIG. 1 is a configuration diagram of an endoscope system according to a first embodiment of the present invention.

In FIG. 1, a reference numeral 1 denotes an endoscope system that includes a scope 2, a light source apparatus 3, a video processor 4, a monitor 5, and a communication cable 6. The scope 2 is an endoscope that applies, to an object, light supplied from the light source apparatus 3, thereby enabling various kinds of observation and treatment to be performed. The scope 2 is connected to the light source apparatus 3 through a light guide connector 15, and is connected to the video processor 4 through a video connector 16.

A proximal end of a light guide 11 that is inserted into the scope 2 is connected to the light guide connector 15, and a distal end of the light guide 11 is extended up to a distal end of an insertion portion of the scope 2. When the light guide connector 15 is connected to the light source apparatus 3, light from the light source apparatus 3 enters an incident end surface of the proximal end of the light guide 11, and light is outputted from an exit surface of the distal end of the light guide 11 at the distal end of the scope 2.

A lens 12 is disposed in an optical path of the exit light at the distal end of the scope 2. The light that has been supplied from the light source apparatus 3 and has been transmitted inside the light guide 11 is applied to the object from the distal end of the insertion portion of the scope 2 through the lens 12. An optical image of the object that is irradiated with the light is taken through an unillustrated objective lens that is disposed at the distal end of the insertion portion of the scope 2, and the optical image is formed on an image pickup device 13 that converts the optical image into an electric signal.

The image pickup device 13 is a solid-state image pickup device such as a CMOS and a CCD, and is configured as a color image pickup device in which a color filter array and the like are disposed, or a monochromatic image pickup device that receives frame-sequential illumination light. The image pickup device 13 converts the optical image of the object into an electric image pickup signal, and transmits, through a signal line 14, the image pickup signal to the video processor 4 to which the video connector 16 is connected.

The video processor 4 processes the image pickup signal received from the image pickup device 13, to generate an image signal for display on a monitor 5. For example, the video processor 4 synchronizes the image pickup signals of respective colors provided from the image pickup device 13 to generate a color image signal. After performing image processing such as color balance adjustment, gamma conversion, and color conversion on the generated image signal, the video processor 4 converts the processed image signal into a signal of a format for display on the monitor 5, and outputs the converted signal to the monitor 5. As a result, the image of the object is displayed on the monitor 5.

Further, the video processor 4 extracts, for example, a luminance signal from the received image pickup signal, and generates brightness information based on the extracted luminance signal. The brightness information thus generated by the video processor 4 is transmitted to the light source apparatus 3 through the communication cable 6 that connects the video processor 4 to the light source apparatus 3.

Next, an internal configuration of the light source apparatus 3 is described. The light source apparatus 3 includes, as a main part, a light emitting section 20, a driving section 50, a control section 100, and an operation panel 110. The light source apparatus 3 can adjust intensity of the light to be supplied to the scope 2, and can supply light that is stable to environmental changes and individual variation.

The light emitting section 20 includes, as a light source portion, a single or a plurality of light sources each generating light to be applied to the object, and supplies the generated light to the scope 2 through the light guide connector 15. As the light source generating light, for example, a light emitting device such as a xenon lamp and an LED is used. As described later, the light emitting section 20 includes an optical sensor 25 (see FIG. 2) that detects intensity of the light emitted by the light source.

The driving section 50 includes a driving circuit that drives the light source of the light emitting section 20, a power supply circuit that supplies stabilized power of a predetermined voltage, and the like. The driving section 50 drives the light emitting device serving as the light source with a predetermined current, voltage, or frequency, thereby causing the light emitting device to generate a predetermined quantity of light. Operation of the driving section 50 is controlled by a control signal provided from the control section 100.

The control section 100 controls the current, the voltage, or the frequency that is supplied to the light source of the light emitting section 20 through the driving section 50, thereby adjusting the intensity of the generated light. For example, the control section 100 varies the current to be supplied to the light source through PWM control, thereby adjusting light emission intensity of the light source. The light intensity adjustment is performed, based on input from the optical sensor 25, based on the brightness information of the object that is acquired in communication with the video processor 4 through the communication cable 6, or based on brightness setting of the illumination light by a user through the operation panel 110.

The operation panel 110 allows the user to perform operation for the light source apparatus 3, and allows for operation such as power on/off of the light source apparatus 3, setting of an observation mode, and the brightness setting of the emission light. When the user operates the operation panel 110 to set a desired observation mode, the set observation mode is transmitted to the video processor 4 through the control section 100 and the communication cable 6, and image processing corresponding to the observation mode is performed by the video processor 4.

Figure 2:
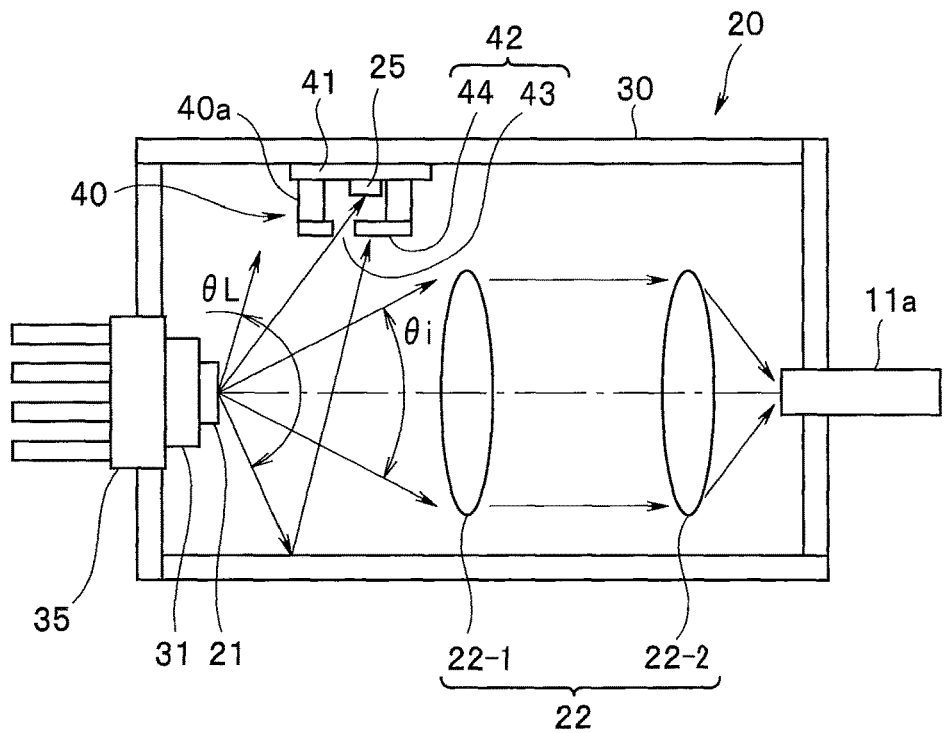
FIG. 2 is an explanatory diagram illustrating a configuration of a light emitting section according to the first embodiment of the present invention.

FIG. 2 illustrates a configuration of the light emitting section 20. In the present embodiment, the light source portion that generates light to be applied to the object is configured of an LED 21. A lens system 22 for light guiding and light condensing is disposed in an optical path of the light emitted from the LED 21. The lens system 22 is an optical portion that receives a portion of the light emitted by the LED 21 and guides the received light, thereby forming an optical path to apply the light to the object. FIG. 2 illustrates an example in which light that has been received by a front lens 22-1 and has been converted into parallel light is condensed by a rear lens 22-2, and the condensed light enters a proximal end of a light guide 11$a$ connected to the light guide connector 15.

The LED 21 and the lens system 22 are housed in an optical case 30 serving as a dustproof first housing. An LED substrate 31 on which the LED 21 is mounted is disposed inside the optical case 30, and a heatsink 35 is in thermal contact with the LED substrate 31. The heatsink 35 is a heat dissipation member to dissipate, to the outside of the optical case 30, heat that is generated in light emission of the LED 21.

Further, the optical sensor 25 serving as a detection portion that detects intensity of the light, is disposed at a position that allows the optical sensor 25 to receive light other than the light entering the lens system 22 out of the light emitted by the LED 21, inside the optical case 30, in order to detect the intensity of the light without inhibiting the quantity of light emitted from the light source. The optical sensor 25 is housed in a dedicated photometric case 40 serving as a second housing. A light guide portion 42 that takes in the light emitted from the LED 21 is provided in the photometric case 40.

More specifically, the optical sensor 25 is attached on a sensor substrate 41 that forms a bottom surface surrounded by a side wall part 40$a$ of the photometric case 40. The light guide portion 42 that takes in the light emitted from the LED 21 is provided on opening side of the side wall part 40$a$. The light guide portion 42 causes direct light from the LED 21 to enter the optical sensor 25, and inhibits scattered light and disturbance light from entering the optical sensor 25.

More specifically, the light guide portion 42 includes a transmission part 43 and a shielding part 44. The transmission part 43 is disposed in an optical path of the light that directly travels from the LED 21 to the optical sensor 25, out of the light emitted by the LED 21 at an angle between a maximum incident angle $\theta i$ of the light to the lens system 22 and a maximum distribution angle $\theta L$ of the light of the LED 21, and allows transmission of the light. The shielding part 44 prevents indirect light that is reflected or scattered inside the optical case 30, out of the light emitted by the LED 21, from entering the optical sensor 25. The side wall part 40$a$ of the photometric case 40 forms a portion of the shielding part 44, and three-dimensionally surrounds the optical sensor 25. As a result, it is possible to remove the indirect light that is varied by influence of environmental change such as ambient temperature, and individual variation for each apparatus, and to accurately detect only the direct light from the LED 21, thereby measuring the light quantity stably and accurately.

In the present embodiment, the shielding part 44 is made of a material that does not allow transmission of light, such as a metal material, and the transmission part 43 is formed as an opening hole surrounded by the shielding part 44. Note that the opening part of the photometric case 40 is covered with a transparent member such as glass or a resin material, and the transparent member may be coated with a material that absorbs or reflects light, or the like. Then, the uncoated part may serve as the transmission part 43, and the coated part may serve as the shielding part 44.

Figure 3:
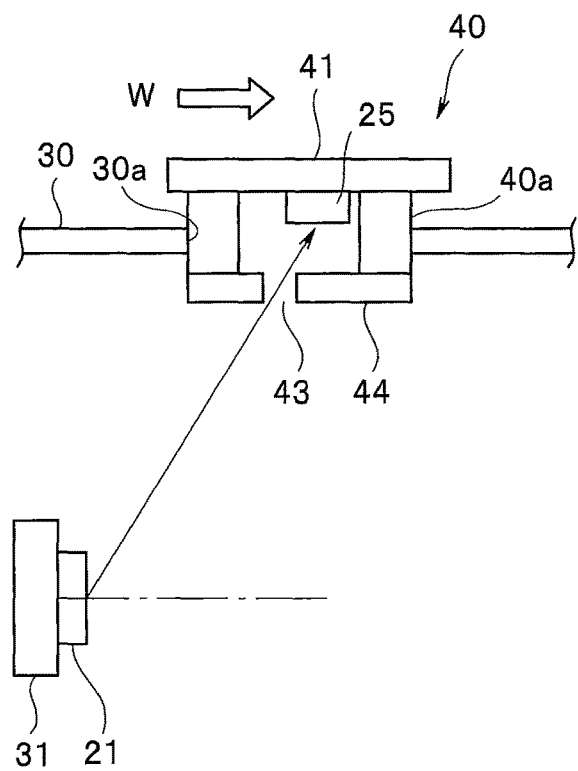
FIG. 3 is an explanatory diagram illustrating a layout example 1 of an optical sensor according to the first embodiment of the present invention.
Figure 4:
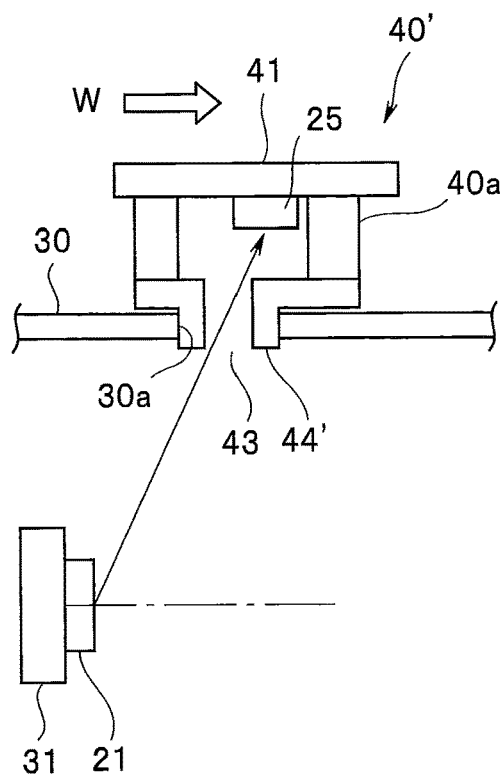
FIG. 4 is an explanatory diagram illustrating a layout example 2 of the optical sensor according to the first embodiment of the present invention.
Figure 5:
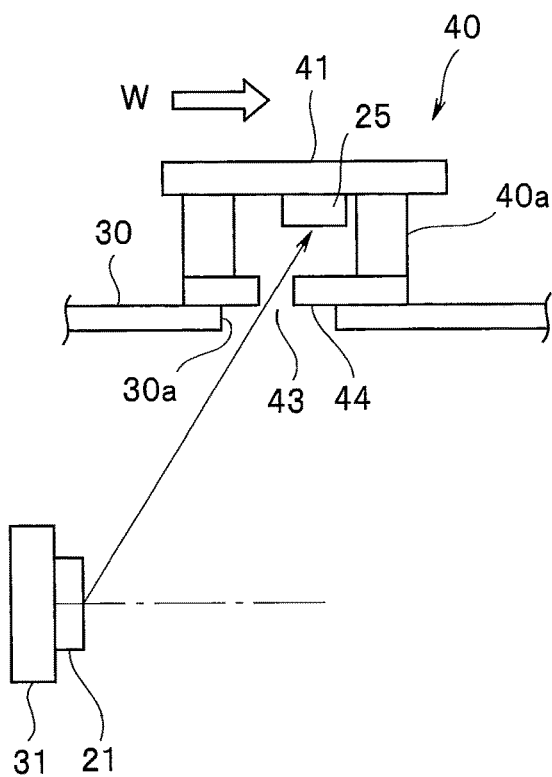
FIG. 5 is an explanatory diagram illustrating a layout example 3 of the optical sensor according to the first embodiment of the present invention.

Here, the optical sensor 25 may be disposed as illustrated in FIG. 3 to FIG. 5, with respect to the optical case 30. FIG. 3 to FIG. 5 each exemplify layout to suppress temperature increase of a peripheral portion of the optical sensor 25 caused by heat from the LED 21.

In a layout example 1 of the optical sensor 25 illustrated in FIG. 3, the sensor substrate 41 on which the optical sensor 25 is mounted is used as a heat transfer portion that can transfer the heat of the optical sensor 25, and is disposed outside the optical case 30. More specifically, an opening part 30$a$ is provided in the optical path of the direct light to the optical sensor 25 of the optical case 30, and the heat transfer portion of the optical sensor 25 is disposed outside the optical case 30 by fitting the side wall part 40a of the photometric case 40 to the opening part 30a to fix the photometric case 40 to the optical case 30.

Such a layout makes it possible to secure a light entering path of the direct light from the LED 21 to the optical sensor 25 while preventing air and dust outside the optical case 30 from flowing into the optical case 30 and the photometric case 40 through the opening part 30a. Further, it is possible to effectively dissipate heat in the periphery of the optical sensor 25 from the sensor substrate 41, by cooling air W outside the optical case 30. As a result, it is possible to prevent deterioration of detection accuracy caused by temperature increase of the optical sensor 25, and to accurately adjust the intensity of the light emitted by the LED 21.

Further, FIG. 4 illustrates a layout example 2 in which a main body portion of a photometric case 40' is disposed outside the optical case 30. The photometric case 40' is changed in shape of the shielding part 44 of the photometric case 40. The photometric case 40' includes a shielding part 44' that projects forward, in contrast to the shielding part 44 of the photometric case 40. A projecting part of the shielding part 44' is fitted and fixed to the opening part 30a provided in the optical case 30 to dispose the main body portion of the photometric case 40' outside the optical case 30.

As a result, similarly to FIG. 3, it is possible to prevent outside air and dust from entering the optical case 30 and the photometric case 40, and to secure the light entering path of the direct light from the LED 21 to the optical sensor 25, which allows for effective dissipation of the heat in the periphery of the optical sensor 25 by the cooling air W.

FIG. 5 illustrates a layout example 3 in which the entire photometric case 40 is disposed outside the optical case 30. The light shielding part 44 of the photometric case 40 is brought into contact with and fixed to the optical case 30 so as to surround a peripheral edge of the opening part 30a provided in the optical case 30. As a result, similarly to FIG. 3, it is possible to prevent outside air and dust from entering the optical case 30 and the photometric case 40, and to secure the light entering path of the direct light from the LED 21 to the optical sensor 25, which allows for effective dissipation of the heat in the periphery of the optical sensor 25 by the cooling air W.

In addition, in the photometric case 40 (40'), the side wall part 40a and the shielding part 44 (44') may be configured as a heat insulation part made of a heat insulation member such as a resin material. This makes it possible to block heat transfer from the optical case 30 and the periphery of the optical case 30 to the optical sensor 25, and to accordingly prevent deterioration of detection accuracy caused by temperature increase of the optical sensor 25.

Next, in a case where a plurality of light sources are adjacently disposed in the optical case 30, layout of the optical sensors 25 provided correspondingly to the plurality of light sources is described.

As described above, the optical sensor 25 is disposed, as a positional condition, at a position between the maximum incident angle of the light to the lens system 22 and the maximum distribution angle of the light of the light source so as not to inhibit the emission quantity of the light from the light source. The lens system 22 guides and condenses the light from the light source. In a case of a single light source, the optical sensor 25 may be provided at any position as long as satisfying the above-described positional condition. In contrast, in a case where the plurality of light sources are adjacently arranged, it is necessary to consider influence of light from the adjacent light source, in the optical sensors 25 that are provided correspondingly to the respective light sources.

Figure 6:
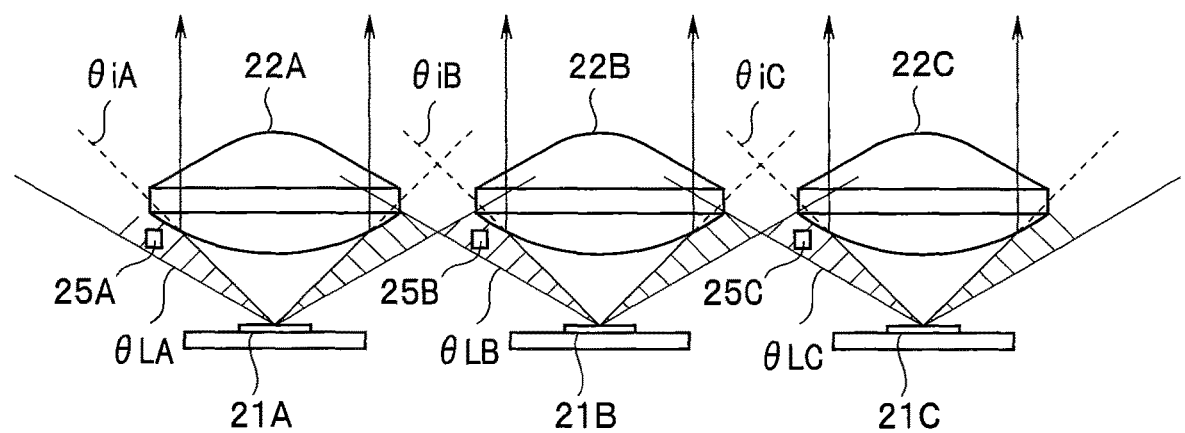
FIG. 6 is an explanatory diagram illustrating a layout example 1 of a transmission part for each light source according to the first embodiment of the present invention.

For example, as illustrated in FIG. 6, in a case where three LEDs 21A, 21B, and 21C are adjacently disposed as the plurality of light sources and influence of the adjacent light source is not ignorable, transmission parts 25A, 25B, and 25C that are provided to detect the light emission intensity of the respective light sources are disposed in respective regions illustrated by hatching in the drawing.

In other words, the transmission parts 25A, 25B, and 25C are disposed in the respective regions between the maximum incident angles θiA, θiB, and θiC of light of the detection-objective light sources to respective lens systems 22A, 22B, and 22C and the maximum distribution angles θLA, θLB, and θLC of light of the respective detection-objective light sources, outside the maximum distribution angle of the adjacent detection-nonobjective light source. Deterioration of the detection accuracy of the transmission parts 25A, 25B, and 25C caused by the influence of the light from the adjacent light source is accordingly prevented.

Further, in a case where influence of feeble scattering light and the like that is present outside the maximum distribution angle of the detection-nonobjective light source is not ignorable, improvement of the detection accuracy is achieved by providing the transmission parts 25A, 25B, and 25C at respective positions allowing for reduction and elimination of the influence.

For example, in a case where the light emission intensity of the respective LEDs 21A, 21B, and 21C are different from one another, when the transmission parts 25A, 25B, and 25C for the respective light sources are disposed such that the transmission part corresponding to the light source having low light emission intensity is adjacent to the transmission part corresponding to the light source having the high light emission intensity, even in the hatching region of FIG. 6, the sensor for the light source having the low light emission intensity is influenced by the disturbance light of the light source having the high light emission intensity, and the detection accuracy of the sensor is accordingly deteriorated.

The sensor is largely influenced by the detection-nonobjective light source in a case where the light source having the low light emission intensity and the light source having the high light emission intensity are adjacent to each other. Therefore, the sensor that detects the light source having the relatively low light emission intensity is provided at a position that is within the hatched region of FIG. 6 and is apart from the light source having the high light emission intensity, which prevents deterioration of the detection accuracy.

Figure 7:
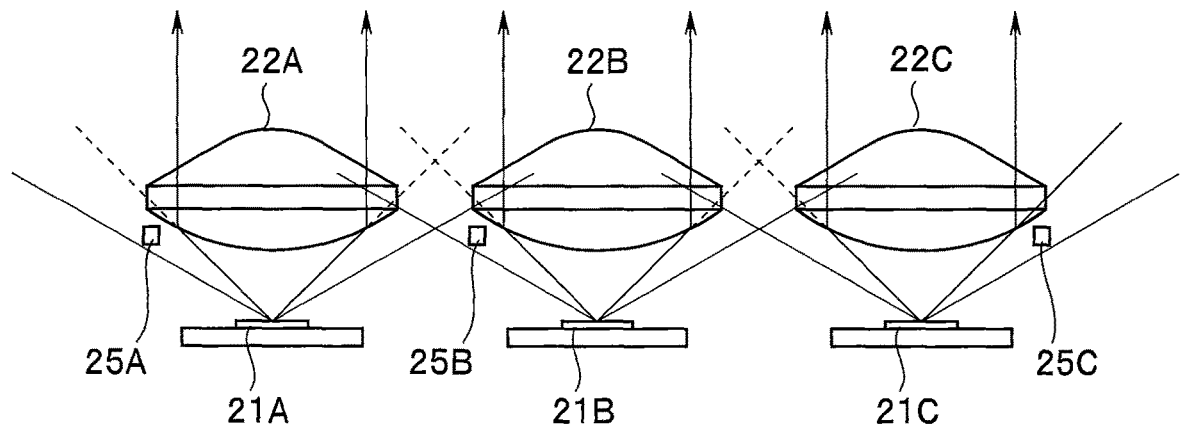
FIG. 7 is an explanatory diagram illustrating a layout example 2 of the transmission part for each light source according to the first embodiment of the present invention.

For example, in a case where the LED 21B has the highest light emission intensity among the LEDs 21A, 21B, and 21C, as illustrated in FIG. 7, the transmission part 25A that is provided to detect the light emission intensity of the LED 21A is disposed at a position apart from the LED 21B, and the transmission part 25C that is provided to detect the light emission intensity of the LED 21C is disposed at a position apart from the LED 21B, with respect to the transmission part 25B that is provided to detect the light emission intensity of the LED 21B. This allows each of the transmission part 25A that is provided to detect the light emission intensity of the LED 21A and the transmission part 25C that is provided to detect the light emission intensity of the LED 21C, to avoid influence of the LED 21B.

Figure 8:
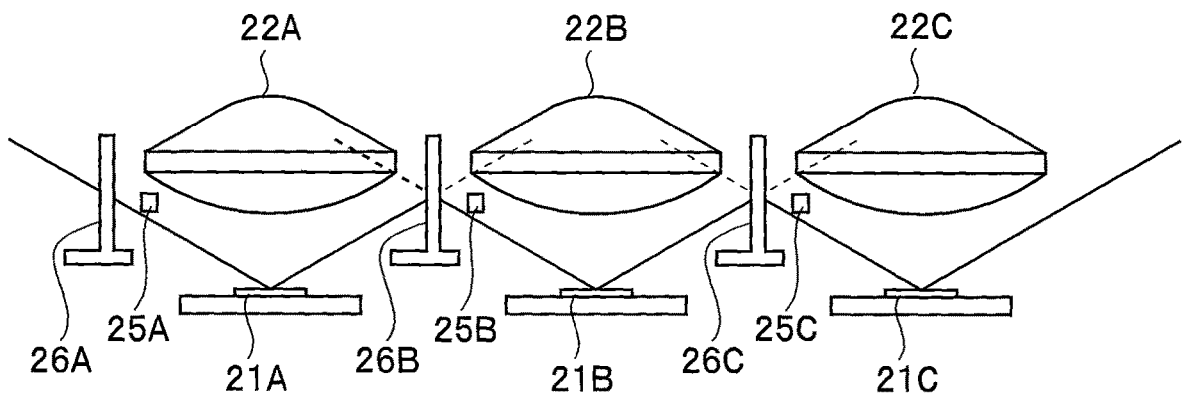
FIG. 8 is an explanatory diagram illustrating an example in which a light shielding plate is provided between the light sources according to the first embodiment of the present invention.
Figure 9:
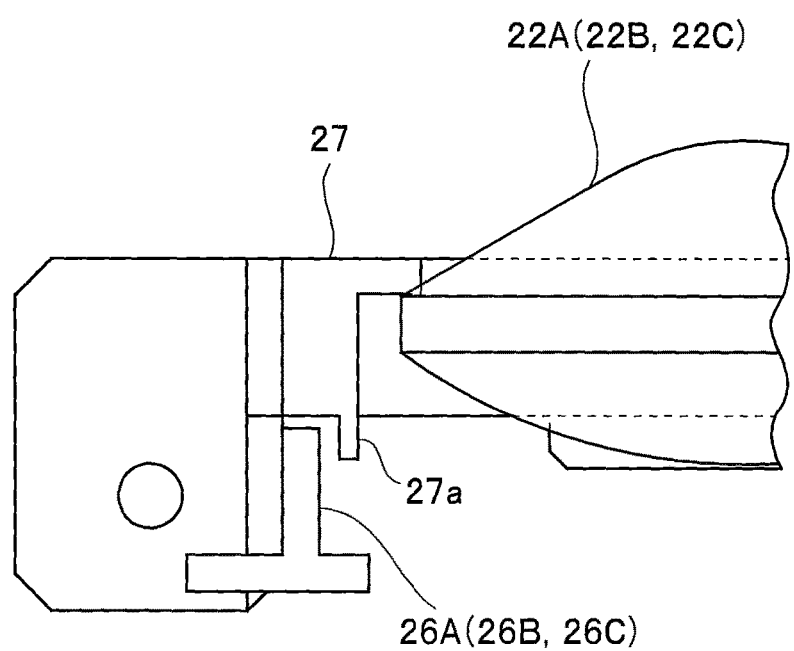
FIG. 9 is an explanatory diagram illustrating the light shielding plate and a lens holding frame according to the first embodiment of the present invention.

In this case, as illustrated in FIG. 8, the detection accuracy may be improved by providing light shielding plates 26A, 26B, and 26C among the adjacent LEDs 21A, 21B, and 21C.

The light shielding plates 26A, 26B, and 26C may be integrally provided in the lens holding frames that respectively hold the lens systems 22A, 22B, and 22C, or may be added as separate components.

In a case where the light shielding plates 26A, 26B, and 26C (hereinafter, collectively referred to as the light shielding plates 26) are provided as the separate components, a protrusion 27a or the like is provided on the lens holding frame 27 and the protrusion 27a is overlapped with each of the light shielding plates 26, which makes it possible to effectively prevent light leakage from a gap between the lens holding frame 27 and each of the light shielding plates 26.

Second Embodiment

Next, a second embodiment of the present invention is described. The light quantity of the LED 21 used as the light source of the light source apparatus 3 is typically adjusted through PWM control with a large current. To perform accurate control without disturbance in a PWM waveform, it is necessary to connect the driving circuit to the LED 21 with low resistance, and the driving circuit board is disposed near the LED 21. In addition, the optical sensor 25 that detects the light emission state of the LED 21 is disposed near the LED 21 for light detection.

When a large current is applied to the LED 21 in such layout, the pattern of the driving circuit board and the driving device become high temperature, and heat flows into the optical sensor 25 located in the vicinity, which may deteriorate the light detection accuracy. Accordingly, in the second embodiment, deterioration of the light detection accuracy is prevented by reducing heat inflow from the driving circuit board driving the LED 21 to the photometric case 40 housing the optical sensor 25 to maintain the optical sensor 25 at a given temperature or lower.

Figure 10:
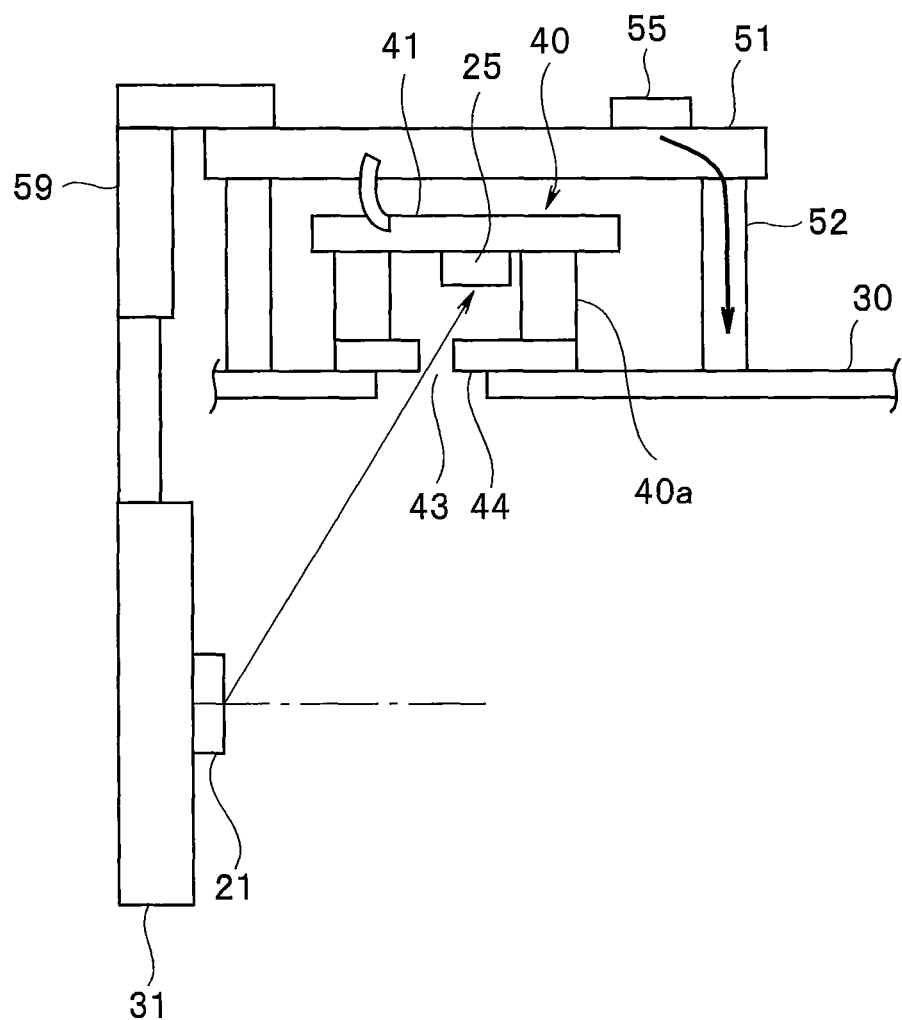
FIG. 10 is an explanatory diagram illustrating layout of a photometric case and a driving circuit board according to a second embodiment of the present invention.

As illustrated in FIG. 10, the photometric case 40 is disposed outside the optical case 30 similarly to FIG. 5, and the driving circuit board 51 that supplies a current to the LED 21 is disposed above the photometric case 40. The driving circuit board 51 is fixed to the outside of the optical case 30 through a substrate support 52, and is disposed with a predetermined interval from the sensor substrate 41 on which the optical sensor 25 is mounted.

The driving circuit board 51 is connected, through a terminal portion 59 with low contact resistance, to the LED substrate 31 on which the LED 21 is mounted, and the LED 21 is driven by the driving device 55 on the driving circuit board 51. The heat generated when the driving device 55 drives the LED 21 is transferred and radiated from the substrate support 52 to the optical case 30 and is dissipated, through a path illustrated by a thick arrow in FIG. 10. This prevents the heat from flowing into the photometric case 40. This makes it possible to suppress temperature increase of the optical sensor 25 and to prevent deterioration of the detection accuracy of the optical sensor 25.

Figure 11:
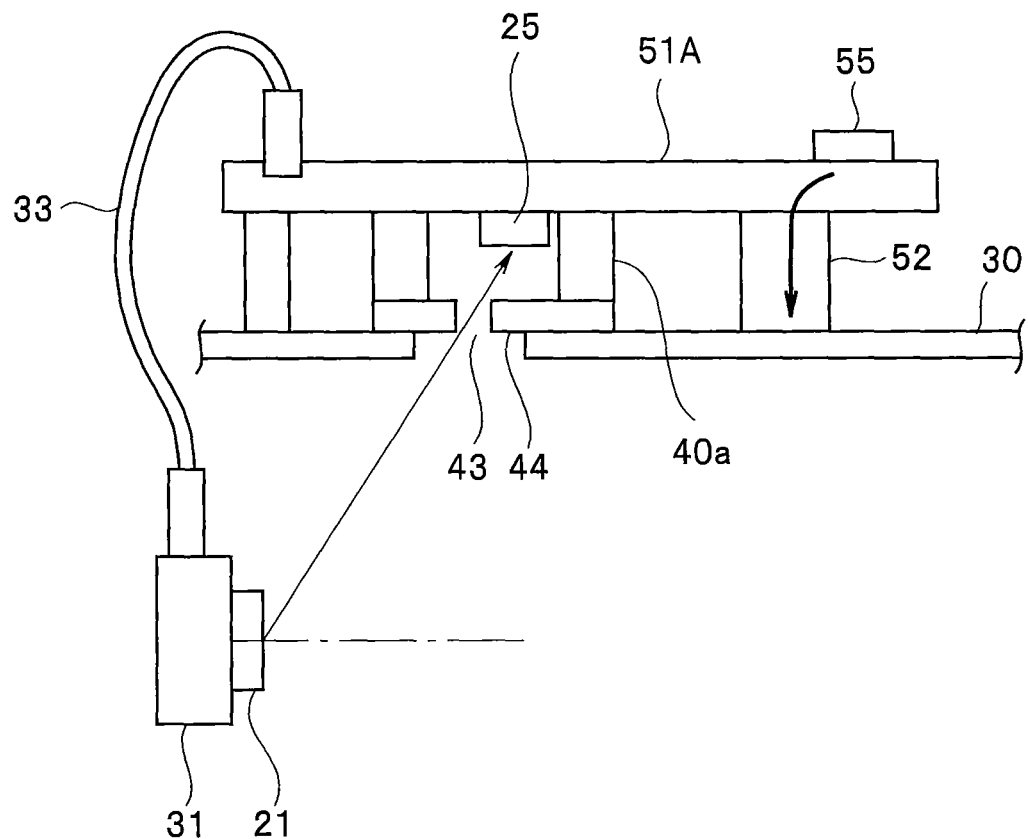
FIG. 11 is an explanatory diagram illustrating an example in which a sensor substrate and the driving circuit board are integrated according to the second embodiment of the present invention.

Note that the sensor substrate 41 of the optical sensor 25 and the driving circuit board 51 may be configured as one circuit board 51A as illustrated in FIG. 11 in order to reduce an attachment space, improve assembling workability, and the like. FIG. 11 illustrates an example in which the circuit board 51A is connected to the LED substrate 31 through an electric cable 33; however, the circuit board 51A may be connected to the LED substrate 31 through the terminal portion 59.

Figure 12:
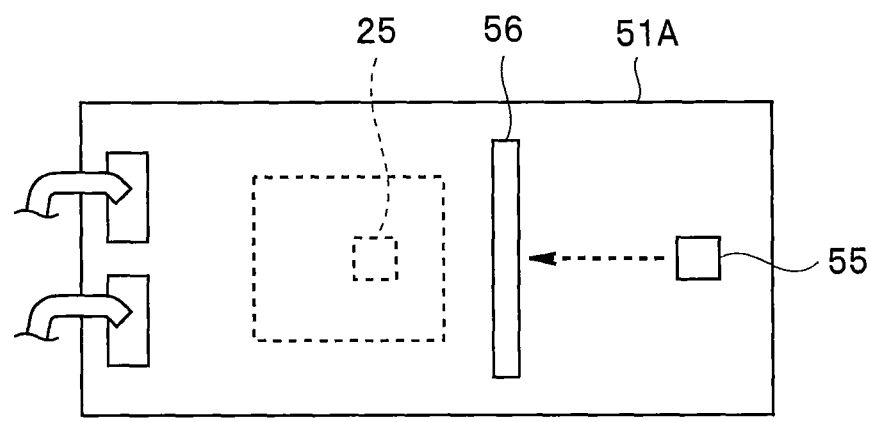
FIG. 12 is a plan view of the circuit board according to the second embodiment of the present invention.

In this case, as illustrated in FIG. 12, a heat conduction prevention portion 56 that prevents heat conduction from the driving device 55 side to the optical sensor 25 side, is provided between the driving device 55 and the optical sensor 25 of the circuit board 51A. The heat conduction prevention portion 56 is formed of an elongated heat insulation member, an air layer of a slit, or the like provided between the driving device 55 and the optical sensor 25 of the circuit board 51A. The heat conduction prevention portion 56 blocks the heat conduction path from the driving device 55 to the optical sensor 25, thereby preventing deterioration of the detection accuracy of the optical sensor 25.

Figure 13:
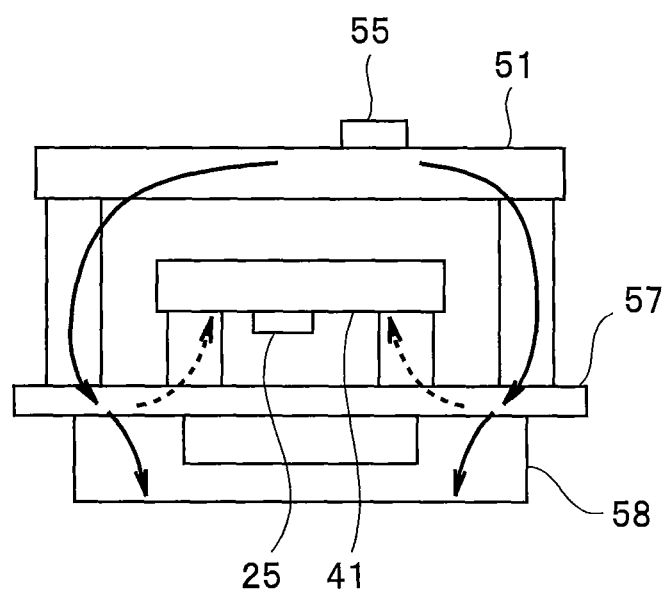
FIG. 13 is an explanatory diagram illustrating a heat conduction path from a driving device according to the second embodiment of the present invention.

Further, as illustrated in FIG. 13, a heat transfer component 57 serving as a heat path may be disposed in every heat conduction path from the driving device 55 to the optical sensor 25, to bring the heat transfer component 57 into thermal contact with a peripheral component 58. This makes it possible to dissipate heat from the driving device 55 to the peripheral component without forming the heat transfer path to the optical sensor 25 side, as illustrated by arrows in FIG. 13, and to accordingly prevent deterioration of the detection accuracy of the optical sensor 25.

In the second embodiment, it is possible to thermally shield the driving device 55 that is the driving heat generation device disposed near the LED 21 and the optical sensor 25 for light detection from each other, and to maintain the temperature of the optical sensor 25 to the given temperature or lower to secure light detection accuracy. As a result, it is possible to accurately adjust the intensity of the light emitted by the LED 21 to maintain a proper light emission state.

Third Embodiment

Figure 14:
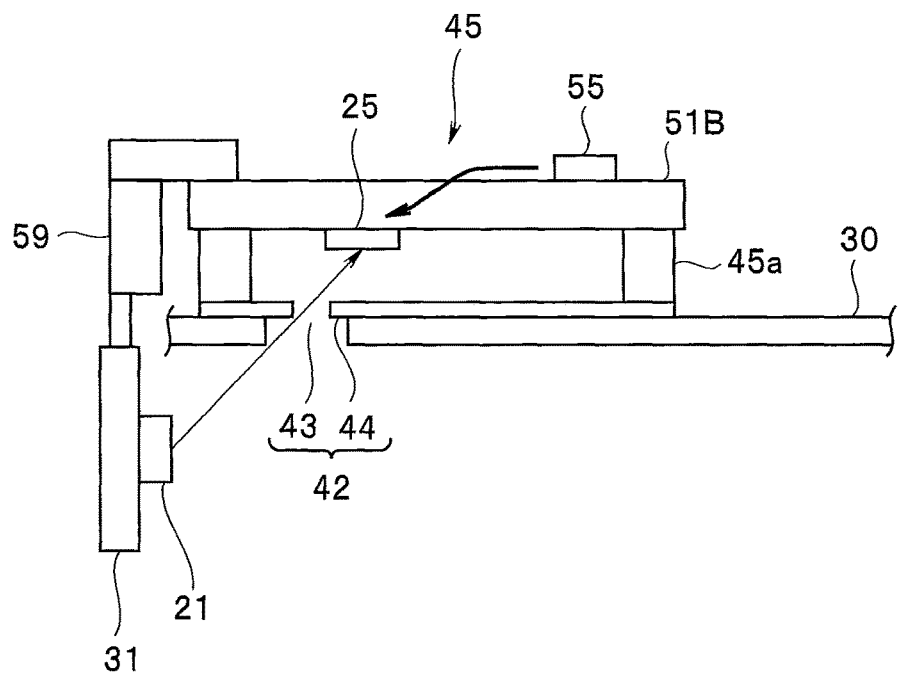
FIG. 14 is an explanatory diagram of a photometric case according to a third embodiment of the present invention.

Next, a third embodiment of the present invention is described. In contrast to the second embodiment, in the third embodiment, the sensor substrate 41 on which the optical sensor 25 is mounted and the driving circuit board 51 also serve as one circuit board 51B, and the circuit board 51B forms a bottom surface part of a photometric case 45 housing the optical sensor 25, as illustrated in FIG. 14.

More specifically, the circuit board 51B of the photometric case 45 according to the third embodiment is held by a side wall part 45a surrounding the optical sensor 25, and the light guide portion 42 to take in the light from the LED 21 is provided on opening side of the side wall part 45a. The light guide portion 42 includes the transmission part 43 and the shielding part 44, similarly to the photometric case 40. The transmission part 43 allows transmission of the direct light that directly enters the optical sensor 25 from the LED 21, and the shielding part 44 blocks indirect light that is reflected or scattered inside the optical case 30, from entering the optical sensor 25. The LED substrate 31 and the circuit board 51B are detachably connected to each other through the terminal portion 59 with low contact resistance.

Figure 15:
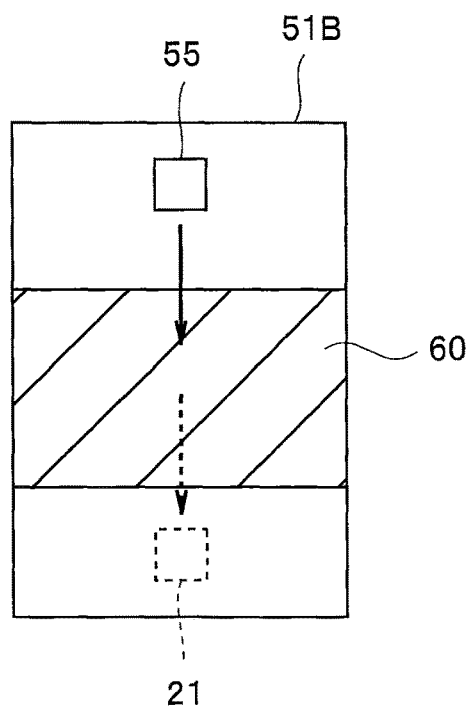
FIG. 15 is an explanatory diagram illustrating an example of a surface ground layer of a circuit board according to the third embodiment of the present invention.

As illustrated in FIG. 15, a surface ground layer 60 for common potential connection is formed on a board surface of the circuit board 51B on the driving device 55 side so as to traverse the heat conduction path between the driving device 55 and the optical sensor 25. The surface ground layer 60 functions as a heat dissipation layer that dissipates heat transferred from the driving device 55 to the surrounding atmosphere. In FIG. 15, the surface ground layer 60 is disposed over a board width between the driving device 55 and the optical sensor 25.

Figure 16:
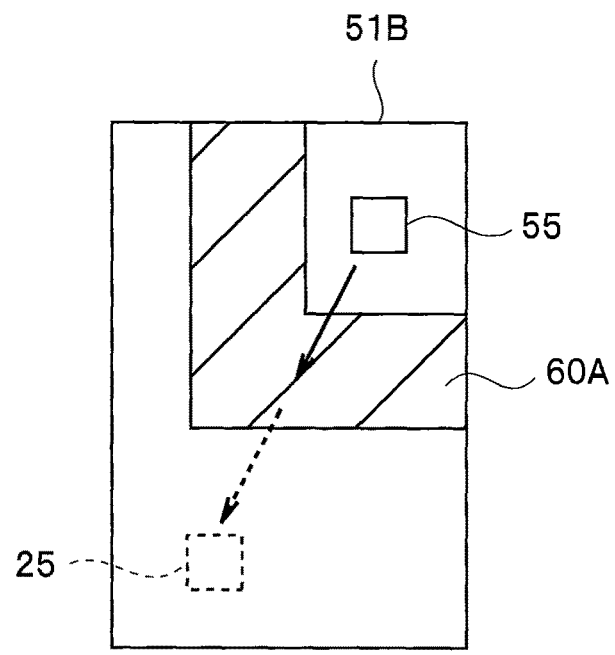
FIG. 16 is an explanatory diagram illustrating another example of the surface ground layer of the circuit board according to the third embodiment of the present invention.

Further, as illustrated in FIG. 16, the surface ground layer 60 may be formed as a surface ground layer 60A that is so disposed as to surround the driving device 55 in two directions inside the circuit board 51B. Moreover, as illustrated in FIG. 17, the surface ground layer 60 may be formed as a surface ground layer 60B that is so disposed as to surround the driving device 55 from four directions.

Figure 17:
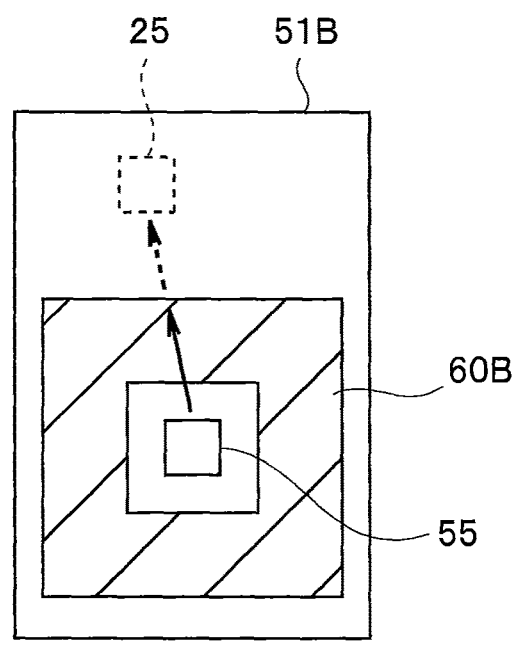
FIG. 17 is an explanatory diagram illustrating still another example of the surface ground layer of the circuit board according to the third embodiment of the present invention.

When the surface ground layer 60 (60A, or 60B) is provided, the heat generated by the driving device 55 is transferred to the surface ground layer 60 (60A, or 60B) as illustrated by a solid arrow in FIG. 15 to FIG. 17, and is dissipated to the surrounding atmosphere. Accordingly, movement of the heat to the optical sensor 25 side as illustrated by a dashed arrow in each of FIG. 15 to FIG. 17 is suppressed, which makes it possible to maintain the optical sensor 25 at the given temperature or lower to secure the light detection accuracy.

Figure 18:
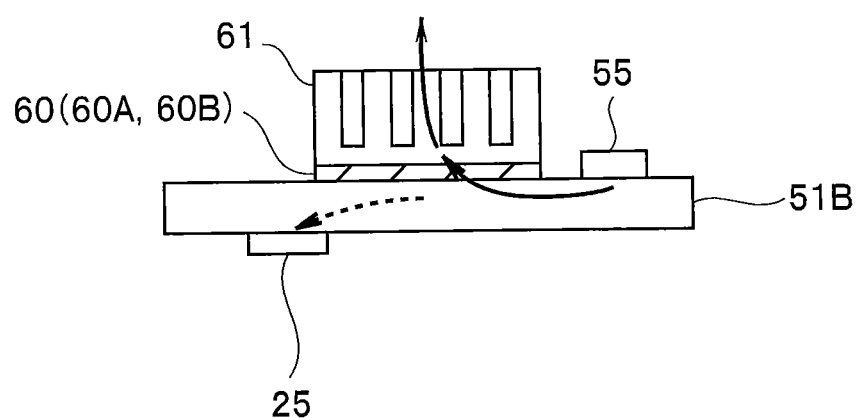
FIG. 18 is an explanatory diagram illustrating an example in which a heat dissipation component is brought into thermal contact with the surface ground layer on driving device side according to the third embodiment of the present invention.
Figure 19:
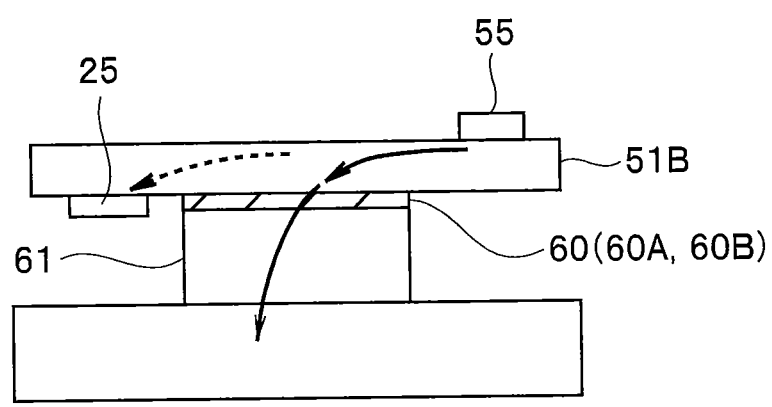
FIG. 19 is an explanatory diagram illustrating an example in which a heat dissipation component is brought into thermal contact with the surface ground layer on optical sensor side according to the third embodiment of the present invention.

In this case, to further promote heat dissipation from the surface ground layer 60 (60A, or 60B), a heat dissipation component 61 made of a heat conduction member or a heat diffusion member may be brought into thermal contact with the surface ground layer 60 (60A, or 60B), as illustrated in FIG. 18 and FIG. 19.

Note that FIG. 18 illustrates an example in which the heat dissipation component 61 is brought into thermal contact with the surface ground layer 60 on the driving device 55 side of the circuit board 51B, and FIG. 19 illustrates an example in which the surface ground layer 60 is provided on the optical sensor 25 side of the circuit board 51B and the heat dissipation component 61 is brought into thermal contact with the surface ground layer 60.

As described above, the heat dissipation component 61 is brought into thermal contact with the surface ground layer 60 (60A, or 60B), which allows for expansion of a heat dissipation area. The heat is dissipated from the heat dissipation component 61 to the surrounding components or the atmosphere, and the movement of the heat to the optical sensor 25 side is suppressed as well, which makes it possible to secure the light detection accuracy of the optical sensor 25.

Also in the third embodiment, it is possible to thermally shield the driving device 55 and the optical sensor 25 that are disposed near the LED 21, to maintain the temperature of the optical sensor 25 to the predetermined temperature or lower to secure detection accuracy, and to maintain the proper light emission state of the LED 21, similarly to the second embodiment.

Here, connection between the LED substrate 31 on which the LED 21 is mounted and the driving circuit board 51 is described. The LED substrate 31 and the driving circuit board 51 are connected to each other through a substrate-mounted terminal in order to reduce electric resistance and to secure quality of a current waveform of the LED 21.

Figure 20:
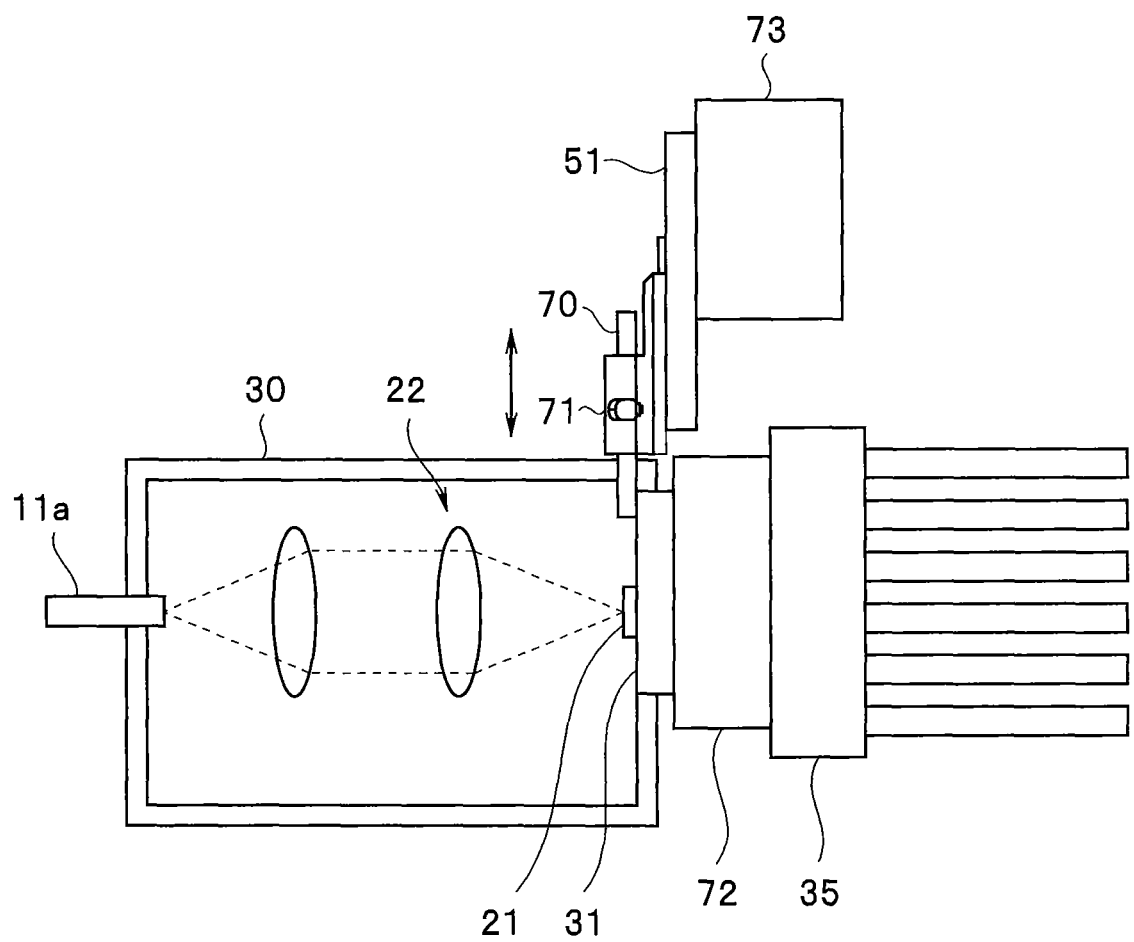
FIG. 20 is an explanatory diagram illustrating connection between an LED substrate and the driving circuit board according to the third embodiment of the present invention.
Figure 21:
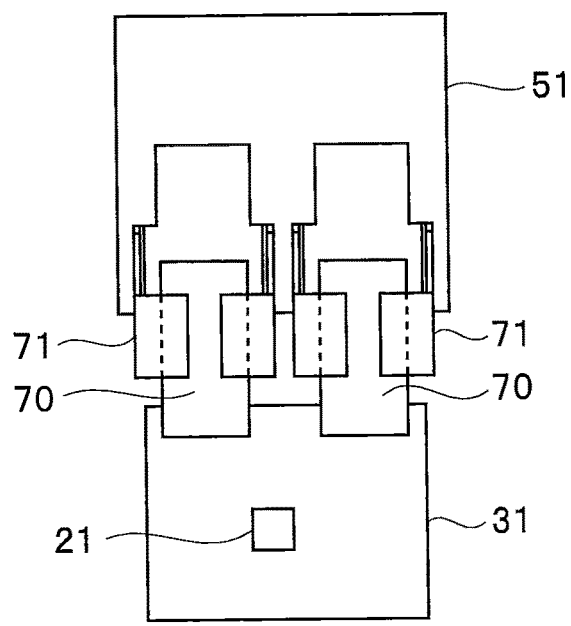
FIG. 21 is a front view of the LED substrate and the driving circuit board according to the third embodiment of the present invention.

For example, as illustrated in FIG. 20 and FIG. 21, a flat tab terminal (a male terminal) 70 is mounted as the substrate-mounted terminal on the LED substrate 31, and a female terminal 71 that is fitted to the flat tab terminal 70 of the LED substrate 31 is mounted on the driving circuit board 51. Further, the male terminal 70 and the female terminal 71 are fitted to each other, for example, in a direction as illustrated by an arrow in FIG. 20, and the LED substrate 31 and the driving circuit board 51 are accordingly electrically connected to each other.

The LED substrate 31 and the driving circuit board 51 that are electrically connected to each other through fitting of the terminals 70 and 71 are fixed to and supported by a predetermined portion outside the optical case 30 inside the light source apparatus 3. The LED substrate 31 is fixed to a first base 72 and is brought into thermal contact with a heatsink 35, and the driving circuit board 51 is fixed to a second base 73.

Figure 22:
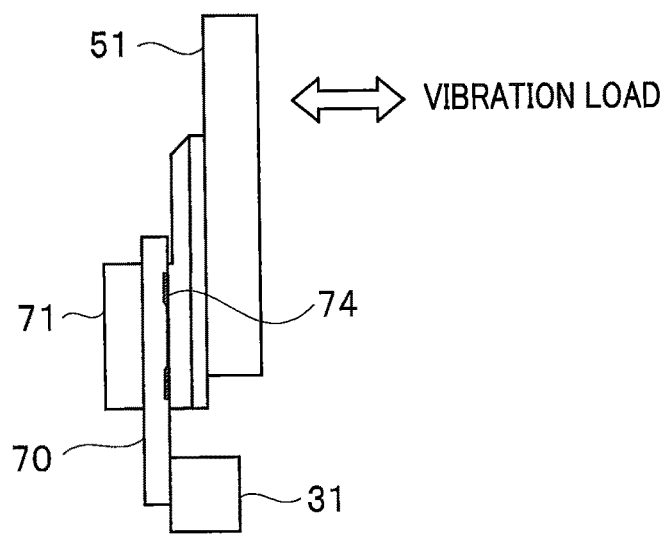
FIG. 22 is an explanatory diagram illustrating an oxide that is generated on a terminal contact surface by vibration according to the third embodiment of the present invention.

When a vibration load is applied to the entire light source apparatus 3 during transportation or the like, however, contact resistance of the terminals 70 and 71 may be increased. For example, as illustrated in FIG. 22, when a vibration load is applied in a direction substantially orthogonal to the fitting direction of the terminals 70 and 71, damage is caused by small slip on a contact surface between the male terminal 70 of the LED substrate 31 and the female terminal 71 of the driving circuit board 51, and an oxide 74 is generated by so-called fretting corrosion. The oxide 74 may increase the contact resistance of the terminals 70 and 71 and may cause failure in the light emission of the LED 21 in some cases.

Figure 23:
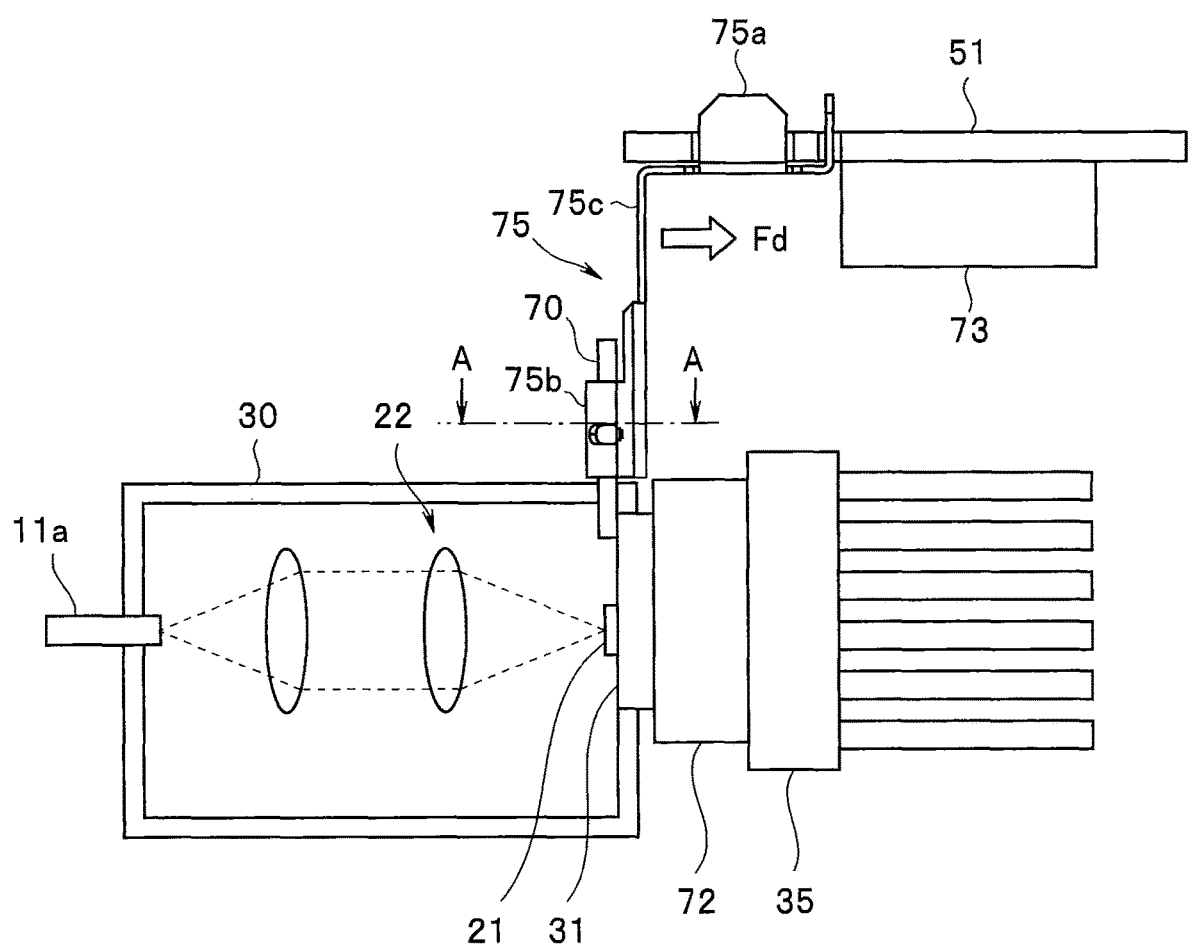
FIG. 23 is an explanatory diagram illustrating connection between the LED substrate and the driving circuit board that copes with vibration load according to the third embodiment of the present invention.

In contrast, connecting the female terminal 71 of the driving circuit board 51 as a female terminal 75 having a shape illustrated in FIG. 23 to the male terminal 70 of the LED substrate 31 makes it possible to prevent increase of the contact resistance at the contact caused by the vibration load. The female terminal 75 includes a mounting part 75a, a fitting part 75b, and a coupling part 75c. The mounting part 75a is fixed to the driving circuit board 51. The fitting part 75b is fitted to the male terminal 70 of the LED substrate 31. The coupling part 75c couples the mounting part 75a with the fitting part 75b.

Figure 24:
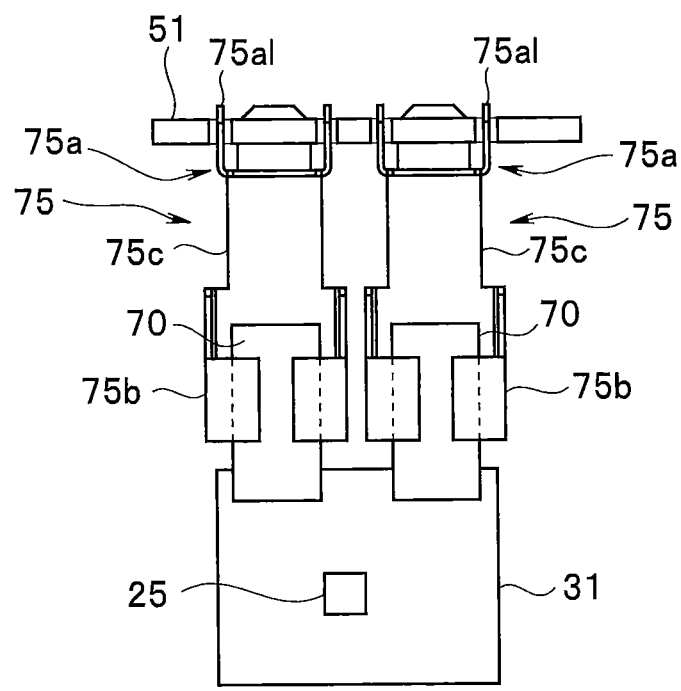
FIG. 24 is an explanatory diagram illustrating a mounting part of a female terminal fixed to the driving circuit board according to the third embodiment of the present invention.

As illustrated in FIG. 24, the mounting part 75a includes a plurality of plate-like protrusion pieces 75a1 that are fitted to the driving circuit board 51. The mounting part 75a is fixed to the driving circuit board 51 through soldering or the like after the protrusion pieces 75a1 are fitted into the driving circuit board 51. The coupling part 75c that couples the mounting part 75a with the fitting part 75b is formed in a flat plate shape, is extended from the fitting part 75b in the same direction as the fitting direction, and is coupled to the mounting part 75a so as to be substantially orthogonal to the driving circuit board 51.

Figure 25:
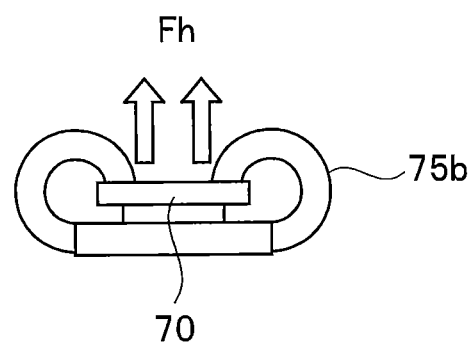
FIG. 25 is a cross-sectional diagram taken along line A-A in FIG. 23 according to the third embodiment of the present invention.

The fitting part 75b that is coupled to the mounting part 75a through such a plate-like coupling part 75c has a shape to sandwich a flat surface part of the male terminal 70 from both sides as illustrated in FIG. 25. The fitting part 75b is set in relationship that pressing force Fh that sandwiches and holds the flat surface part of the male terminal 70 becomes larger than force Fd applied to the coupling part 75c when receiving the vibration load (Fh>Fd).

When the fitting part 75b is set in such relationship, the coupling part 75c is deformed and displaced with smaller force prior to the fitting part 75b, and displacement and abrasion between the male terminal 70 and the female terminal 71 on the surface of the fitting part are reduced, which makes it possible to prevent increase of the contact resistance caused by corrosion of the contact surface even in a case where the first base 72 to which the LED substrate 31 is fixed and the second base 73 to which the driving circuit board 51 is fixed are relatively swung by the vibration load.

As a result, it is possible to prevent lighting failure of the LED 21 even if the vibration load is applied to the electrical connection part between the LED substrate 31 and the driving circuit board 51. Further, setting the fitting direction of the female terminal 71 connected to the male terminal 70 of the LED substrate 31 to the direction perpendicular to the driving circuit board 51 allows for arrangement of the driving circuit board 51 in the direction along the optical case 30, which makes it possible to downsize the entire apparatus.

What is claimed is:

1. A light source apparatus, comprising:
   a light source portion including a first light source and a second light source, the first light source emitting light applied to an object, the second light source emitting light applied to the object and being higher in light emission intensity than the first light source;

a first optical portion configured to receive a portion of the light emitted by the first light source, and to form an optical path to apply the received light to the object;

a second optical portion configured to receive a portion of the light emitted by the second light source, and to form an optical path to apply the received light to the object;

a detection portion that is disposed at a position allowing the detection portion to receive light other than the light received by the first optical portion, out of the light emitted by the first light source, and is configured to detect intensity of the received light;

a shielding part that is disposed between the first light source and the detection portion, to block indirect light from entering the detection portion, and is configured to block the light, the indirect light being generated by reflection or scattering of the light emitted by the first light source; and a transmission part that is disposed at a position apart from the second light source with respect to the first light source in an optical path of light that directly enters the detection portion out of the light within a maximum distribution angle of the first light source, and is configured to allow transmission of the light.

2. The light source apparatus according to claim 1, wherein the light source portion includes a plurality of light sources that are disposed adjacently to one another, and the transmission part that is provided correspondingly to each of the plurality of light sources is disposed in a region between a maximum incident angle of light of a detection-objective light source to the optical portion and a maximum distribution angle of the light of the detection-objective light source, outside a maximum distribution angle of light of an adjacent detection-nonobjective light source.

3. The light source apparatus according to claim 1, wherein the shielding part is configured to three-dimensionally surround the detection portion.

4. The light source apparatus according to claim 1, wherein the detection portion and a driving device that drives the light source portion are disposed on a same substrate, and a heat dissipation layer that traverses a heat conduction path between the driving device and the detection portion, is formed on the substrate.

5. The light source apparatus according to claim 4, wherein a heat dissipation component made of a heat conduction member or a heat diffusion member is brought into thermal contact with the heat dissipation layer.

6. A light source apparatus, comprising:

a light source portion configured to emit light applied to an object;

an optical portion configured to receive a portion of the light emitted by the light source portion, and to form an optical path to apply the received light to the object;

a detection portion that is disposed at a position allowing the detection portion to receive light other than the light received by the optical portion, out of the light emitted by the light source portion, and is configured to detect intensity of the received light;

a transmission part including an opening part in an optical path of the light directly entering the detection portion, out of light within a maximum distribution angle of the light source portion;

a shielding part disposed between the light source portion and the detection portion to block indirect light from entering the detection portion, the indirect light being generated by reflection or scattering of the light emitted by the light source portion;

a housing in which the light source portion and the optical portion are disposed; and a heat transfer portion that is configured to transfer heat of the detection portion and is disposed outside the housing.

7. The light source apparatus according to claim 6, wherein the detection portion is provided outside the housing, the housing includes an opening in the optical path of the light directly entering the detection portion, and the shielding part is provided to surround the opening to prevent air outside the housing from flowing into inside of the housing through the opening.

8. The light source apparatus according to claim 6, wherein the detection portion is provided outside the housing, the housing includes an opening in the optical path of the light directly entering the detection portion, and the shielding part is provided to be fitted to the opening, to prevent air outside the housing from flowing into inside of the housing through the opening.

9. A light source apparatus, comprising:

a light source portion configured to emit light applied to an object;

an optical portion configured to receive a portion of the light emitted by the light source portion, and to form an optical path to apply the received light to the object;

a detection portion that is disposed at a position allowing the detection portion to receive light other than the light received by the optical portion, out of the light emitted by the light source portion, and is configured to detect intensity of the received light;

a transmission part including an opening part in an optical path of light directly entering the detection portion, out of light within a maximum distribution angle of the light source portion; and a shielding part disposed between the light source portion and the detection portion to block indirect light from entering the detection portion, the indirect light being generated by reflection or scattering of the light emitted by the light source portion, wherein a substrate on which the detection portion is mounted and a substrate on which a driving device driving the light source portion is mounted are electrically connected to each other through fitting of terminals of the respective substrates, and one of the terminals of the respective substrates includes a fitting part, a mounting part, and a coupling part, the fitting part being fitted to another terminal, the mounting part being mounted on the substrate, and the coupling part coupling the fitting part with the mounting part and being displaced with smaller force than force of the fitting part by vibration load.

* * * * *